US012766313B2

(12) United States Patent
Franke et al.

(10) Patent No.: US 12,766,313 B2
(45) Date of Patent: Oct. 20, 2026

(54) EXTENSION OF A PREVIOUSLY IMPLANTED LEAD OR ELECTRODE

(71) Applicant: NEURONOFF, INC., Cleveland, OH (US)

(72) Inventors: Manfred Franke, Cleveland, OH (US); John Wardle, Cleveland, OH (US); Stephan Nieuwoudt, Cleveland, OH (US); Emily Szabo, Cleveland, OH (US); Shaher Ahmad, Cleveland, OH (US)

( * ) Notice: Subject to any disclaimer, the term of this patent is extended or adjusted under 35 U.S.C. 154(b) by 281 days.

(21) Appl. No.: 18/292,852

(22) PCT Filed: Jul. 28, 2022

(86) PCT No.: PCT/US2022/038719

§ 371 (c)(1),
(2) Date: Jan. 26, 2024

(87) PCT Pub. No.: WO2023/009750

PCT Pub. Date: Feb. 2, 2023

(65) Prior Publication Data

US 2024/0269462 A1 Aug. 15, 2024

Related U.S. Application Data

(60) Provisional application No. 63/226,465, filed on Jul. 28, 2021.

(51) Int. Cl.
*A61N 1/05* (2006.01)
*A61N 1/04* (2006.01)
*A61N 1/375* (2006.01)

(52) U.S. Cl.
CPC ........... *A61N 1/0551* (2013.01); *A61N 1/048* (2013.01); *A61N 1/0488* (2013.01); *A61N 1/375* (2013.01); *A61N 1/3752* (2013.01); *A61N 1/3754* (2013.01)

(58) Field of Classification Search
CPC .... A61N 1/0551; A61N 1/048; A61N 1/0488; A61N 1/375; A61N 1/3752; A61N 1/3754
See application file for complete search history.

(56) References Cited

U.S. PATENT DOCUMENTS 8,600,507 B2 * 12/2013 Brase .................. A61N 1/3752 439/668
10,201,713 B2 * 2/2019 Leven ..................... A61N 1/05
2003/0077943 A1 * 4/2003 Osypka .................. H01R 31/02 439/623
2006/0015163 A1 * 1/2006 Brown ................... A61N 1/056 607/116
2008/0103552 A1 * 5/2008 Goetz ................ A61N 1/37247 607/2
2020/0346021 A1 * 11/2020 Nageri ................ A61N 1/3752

* cited by examiner

*Primary Examiner* — Amanda K Hulbert
(74) *Attorney, Agent, or Firm* — Joel Douglas; Thomas Ciesco; Jeffrey Semprebon

(57) ABSTRACT

A system and methods and disclosed for extending a previously implanted lead for connecting to an internal pulse generator (IPG), or for extending the lead to a new tissue target.

4 Claims, 13 Drawing Sheets

EXTENSION OF A PREVIOUSLY IMPLANTED LEAD OR ELECTRODE

CROSS-REFERENCE TO RELATED APPLICATIONS

This application is a national phase entry of international application PCT/US22/38719 filed on Jul. 28, 2022 and claims priority to, and the full benefit of, U.S. provisional patent application No. 63/226,465 filed on Jul. 28, 2021.

FIELD OF THE INVENTION

The field of the invention is the use of an implanted lead or electrode to transfer energy to a tissue target.

BACKGROUND

Neuromodulation devices with a lead to a tissue target still face patient and clinician adoption hurdles. The trial lead is a major effort to demonstrate for a patient the potential result of a permanently implanted device. The trial lead is stimulated by various means, often from outside the body. The current trial lead is a temporary lead, often connected to an external pulse generator percutaneously. The trial lead is implanted surgically or otherwise and then removed from the body after a period of days. The patient and clinician then consider the desirability of implanting a permanent lead which would be connected to an implanted internal pulse generator (IPG). If the patient elects to have a permanent lead, a second surgical procedure is required for implanting a second lead at the tissue target. This scenario requires two procedures in which a permanent lead ends up implanted at the tissue target. Disturbing the tissue with a surgical procedure a second time can irritate that tissue and the second procedure also subjects the patient to infection risk. And, of course, the second procedure creates more expense.

SUMMARY

A system and method are provided for implanting at least one lead which can serve as the trial lead for a short period and then remain in place if the patient and clinician so choose: that is, the previously implanted lead can be extended and connected to an IPG or other device.

A system for extending a previously placed lead or electrode for transferring energy to at least one tissue target can comprise at least one primary lead having distal and proximal ends, with a primary connector attached to each proximal end, and at least one secondary lead having first and second ends, with a complementary connector attached to each first end and a secondary connector attached to each said second end such that, when the distal end is positioned near at least one tissue target and the primary and complementary connectors are joined, the system is able to provide at least one completed connection to an internal pulse generator (IPG) or other device. The system may further comprise a return for each such completed connection. The system may comprising a plurality of primary leads and secondary leads, wherein at least a portion of each of the secondary leads is insulated and the secondary leads and the insulated portions are joined together and the secondary connectors are located on a housing or insertion pin.

A device may comprise a primary lead having distal and proximal ends with a primary connector attached to the proximal end, the device being configured for injecting fully into a body through a delivery device. The device can be further configured such that the distal end may be placed near a tissue target, and the proximal end can be configured to pick up energy from a source internal or external to the body as a trial lead, with the primary connector being available to be connected to a complementary connector.

A device may comprise at least one secondary lead having first and second ends, with a complementary connector attached to each first end and a secondary connector attached to each second end and configured for connection to an IPG or other device. The complementary connector can be configured to connect to a primary connector on a proximal end of a primary lead previously placed in a body.

BRIEF DESCRIPTION OF THE FIGURES

FIG. 1A is an embodiment with a single primary and a single secondary lead. FIG. 1B is an embodiment with two sets of primary and second leads. FIG. 1C has four sets of primary and secondary leads. FIG. 1D is similar to FIG. 1C but with returns co-located with each of the secondary leads.

DETAILED DESCRIPTION

Figure 1A:
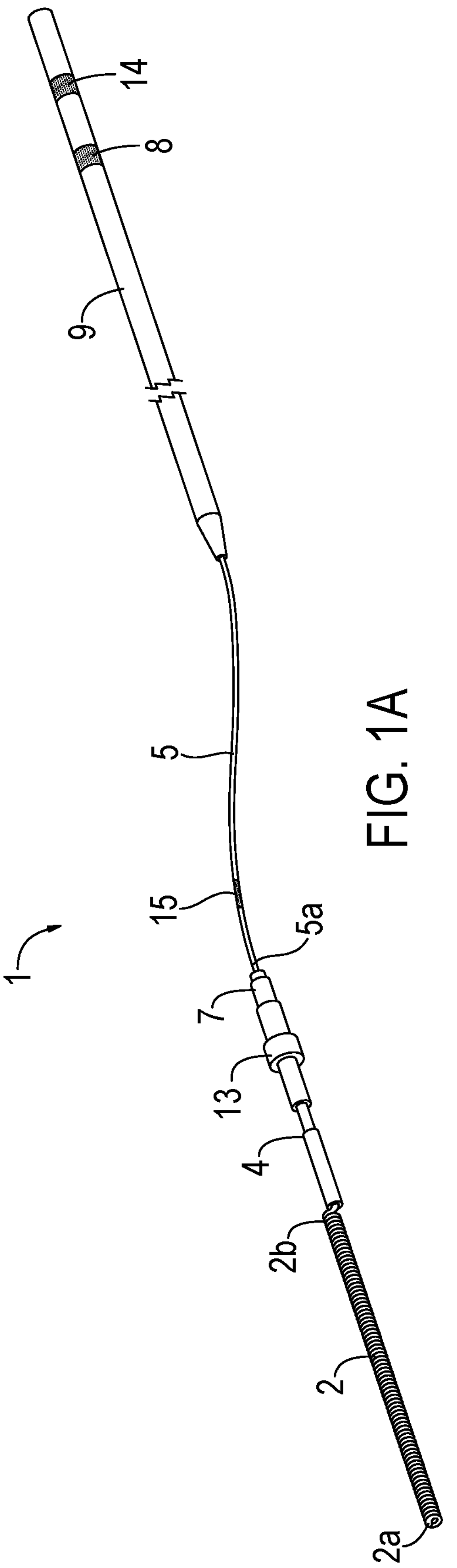
FIGS. 1A-1D are perspective views of various embodiments of the system herein with a pin for connecting to a device with a socket, e.g., an IPG.

The present system and method enable the clinician to convert a previously implanted trial lead to a permanent lead so that the previously implanted lead can remain in place and be connected to an IPG or other device and be used as a permanent lead for a fully implanted and permanent system. A lead which is well adapted to be the primary lead as used herein is the helical wire rope structure electrode as described in PCT/US2021/33007 (hereafter referred to as PCT '007) and which is fully adopted and incorporated as if set forth entirely herein. PCT '007 does not disclose connecting the primary lead 2 to an IPG 3 or other devices. Additionally, the system can also comprise traditional leads which existed prior to that disclosed in PCT '007.

The system and method disclosed herein enable the clinician to convert a previously-implanted trial lead to a permanent lead. First, at least one lead 1 has been previously implanted as a trial lead in accordance with the disclosure in PCT '007 and can be powered with an external power source either through a percutaneous tail extending through the skin, or with a transcutaneous connection enabled by a collector just under the skin. If the patient elects for implantation of a permanent system, then the physician makes an incision near the proximal end of the lead, connects the proximal end to another lead or to another device. There are numerous methods for these other leads and/or devices to be placed, as approved by regulatory bodies and as performed by clinicians.

Beyond the description of primary lead 2 shown in PCT '007, the primary lead can be provided with a "pin" connector end (elements 4 and 17 in FIGS. 6A-6D) which can be passed through the same delivery needle as the helical wire rope structure electrode (element 2 in FIGS. 6A-6D). During the trial period, electrical energy may be coupled directly into the pin 4 placed in the subcutaneous tissue or, alternatively, a secondary helical wire rope structure with a socket (elements 7 and 13 in FIGS. 6A-6D) may be reversibly connected to the needle delivered first helical wire rope structure with a pin. The latter option may provide a larger charge injection interface for improved subcutaneous coupling as compared to the pin only version.

Each primary lead has its own primary connector on its proximal end. With, say, a socket connector on its proximal end, this primary connector may then be connected to a pin (complementary connector) attached to a lead to one of the following: a commercially available adapter, an IPG, any other type of stimulator, or a helical wire rope structure.

Various embodiments of the system comprise a primary connector which is secured to the proximal end of a primary lead before it is implanted as a trial lead. The primary connector may comprise an internal cavity configured to receive and trap an expanding feature on a dockable connector on a separate secondary lead connected to the IPG, and may also comprise a seal integrated at the entry of the docking cavity to prevent tissue ingrowth and preserve the integrity of the interface.

Each type of indirect connection can be enclosed within a sheath, that is, a sacrificial sleeve, to be pierced or removed prior to placement of the complementary connector which inhibits cellular or fluid entry and maintain a connector for future mating.

The primary lead herein may be connected to a primary connector by an element which is selected from the group consisting of a boa-spring, a loop-through, and/or a direct welded connection to the primary lead or parts thereof to secure the primary lead electrically and mechanically to the indirect connector.

Figure 1E:
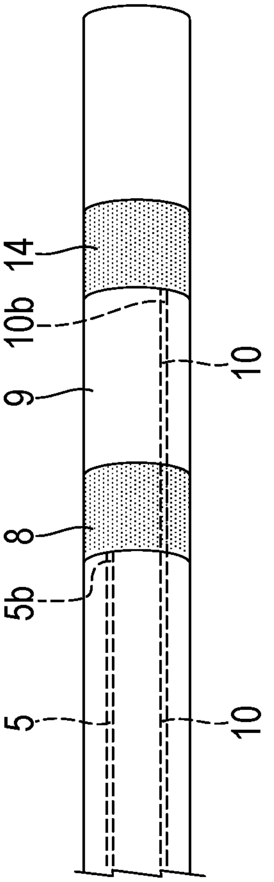
FIG. 1E shows a schematic connection between the return and the contacts on the housing or insertion pin in FIG. 1A.
Figure 1B:
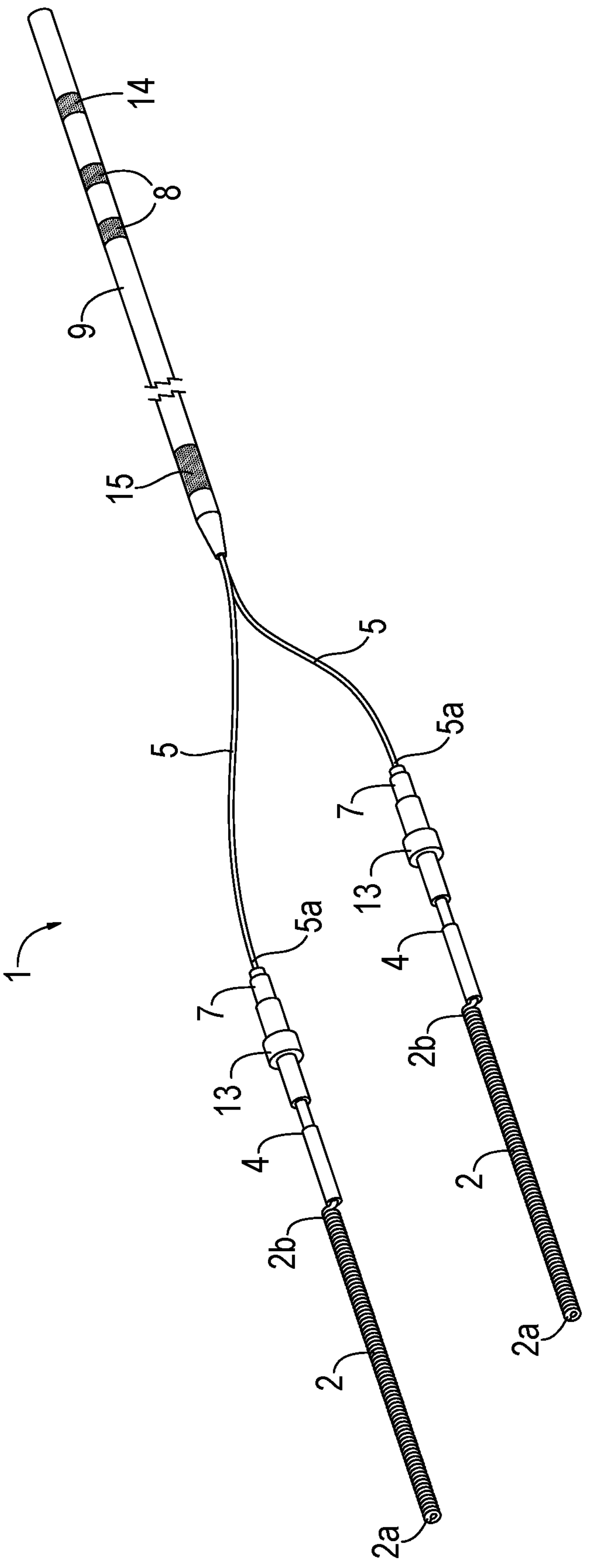
Figure 1C:
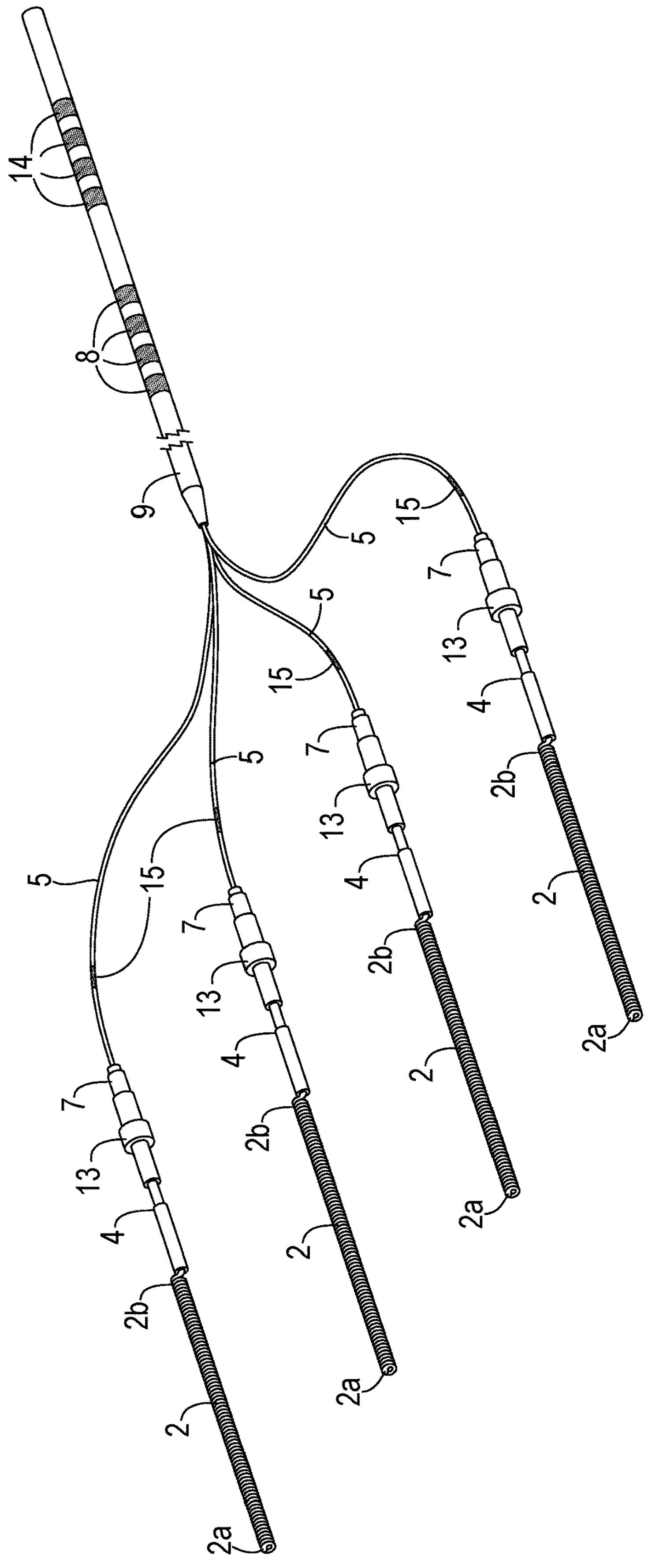
Figure 1D:
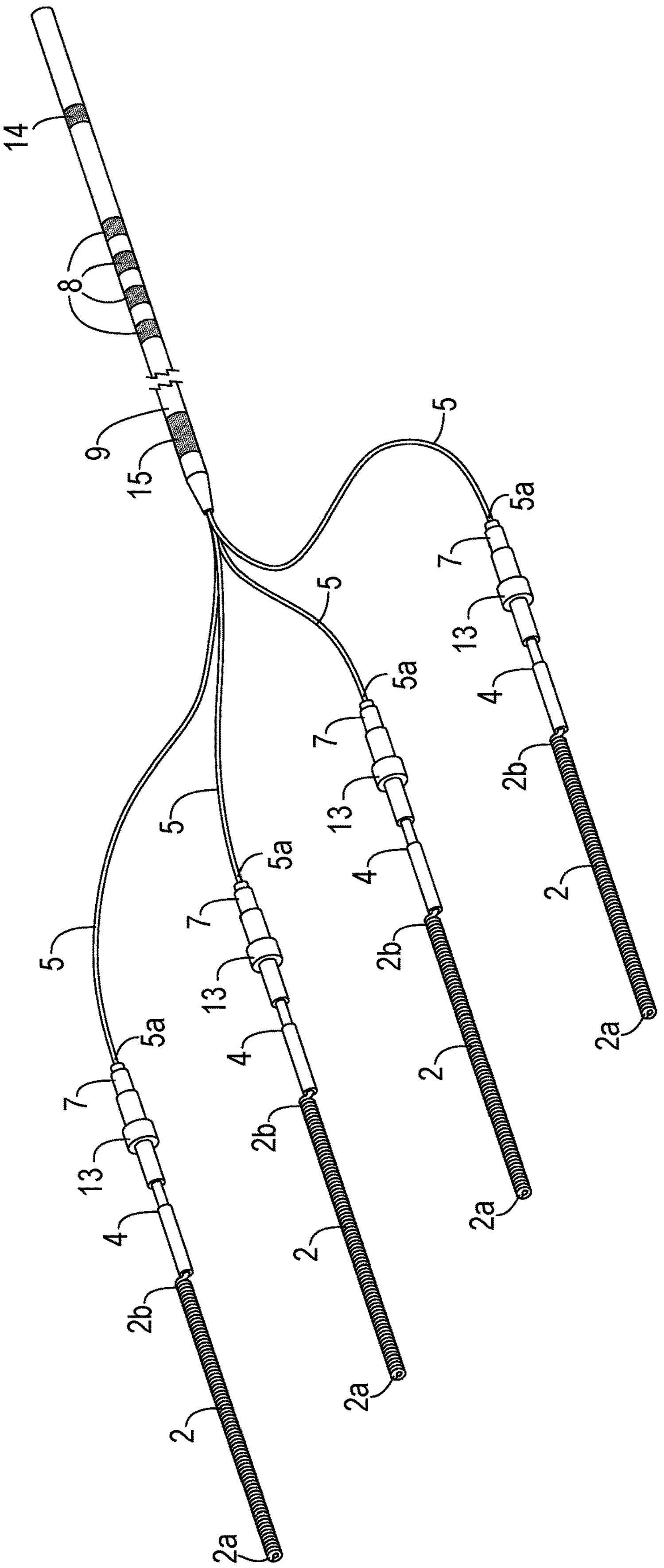

The system 1 herein in FIGS. 1A-1D is depicted in embodiments with the primary lead being a helical wire rope structure, although other embodiments of the system incorporate a traditional wire lead, i.e., non-helical wire rope structure. All of the embodiments shown in FIGS. 1A-1D are perspective views of the system with a pin for insertion into a socketed device such as an IPG. FIG. 1A is an embodiment with a single primary and a single secondary lead. FIG. 1B is an embodiment with two primary and two secondary leads. FIG. 1C has four sets of primary and secondary leads with a pin connected to an IPG having a socket. FIG. 1D is a perspective of a similar set up with returns co-located on each of the secondary leads. Other embodiments, not shown, allow connections for more than four sets of primary and secondary leads to an IPG. In all these embodiments, the diameter of the primary connector is small enough to be injected through a cannula (e.g., 14-20 ga) with the primary lead, in one embodiment the diameter being 1 mm or less. In these embodiments, the system is configured to transfer energy from an IPG or other device to at least one tissue target wherein the system comprises at least one primary lead 2 having distal and proximal ends 2*a*, 2*b*, a primary connector 4 attached to each said proximal end, at least one secondary lead 5 which may be insulated except at its first and second ends 5*a*, 5*b*, a complementary connector 7 attached to each said first end, and a secondary connector 8 attached to each said second end such that, when the distal end is positioned near said at least one tissue target and the primary and complementary connectors are joined, the system is able to provide at least one completed electrical connection between a tissue target and an IPG. Each secondary lead may, in some embodiments, be grouped into a larger housing or insertion pin 9 for connecting to the IPG. A return 10 has one end 10*a* connected to a contact 15 and another end 10*b* connected to a return secondary connector 14. The primary and complementary connectors can be any shape and design so that each connects to the other securely. For example, the primary connector can be a socket and the complementary connector can be a pin, and vice versa, and other designs can be employed in other embodiments. FIG. 1E depicts one embodiment of the secondary connector 8 connected to the second end 5*b* of the secondary lead 5 and the return secondary connector 14 connected to an end 10*b* of the return 10.

Figure 2:
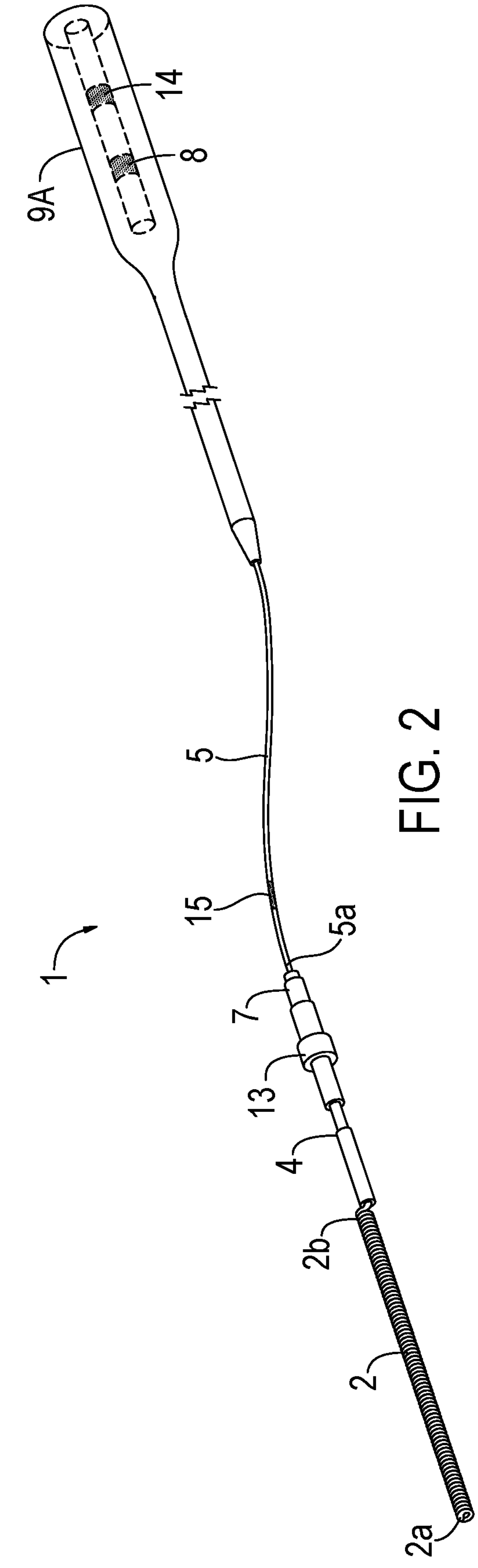
FIG. 2 is a perspective view of an embodiment of the system with a socket for connecting to a lead with a pin.
Figure 2A:
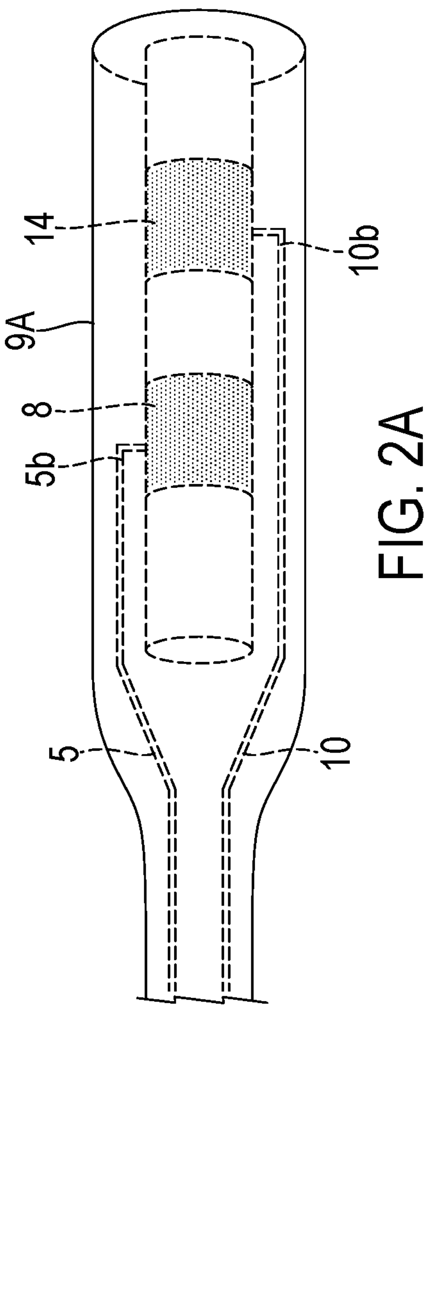
FIG. 2A is a closer view of the socket.

FIG. 2 is a perspective view of an embodiment of the system with a socket for connecting to a pin device such as a lead, and FIG. 2A is a closer view of the socket. The difference between FIG. 1A and FIGS. 2 and 2A is that the insertion pin 9 of FIG. 1A is replaced with a socket 9A, and all other elements of FIGS. 2 and 2A are the same as labeled in FIG. 1A. That is, the embodiment shown in FIG. 2 can connect to a pin of another device such as a previously implanted lead. Other embodiments, not pictured, have multiple primary and second leads which are the same as the single primary and second lead of FIG. 2. These other embodiments would be similar to those shown in FIGS. 1B, 1C and 1D, except that a socket 9A is attached instead of a pin as in FIGS. 1A-1D. FIG. 2A demonstrates schematically that the secondary lead 5 is connected to secondary connector 8.

Figure 3:
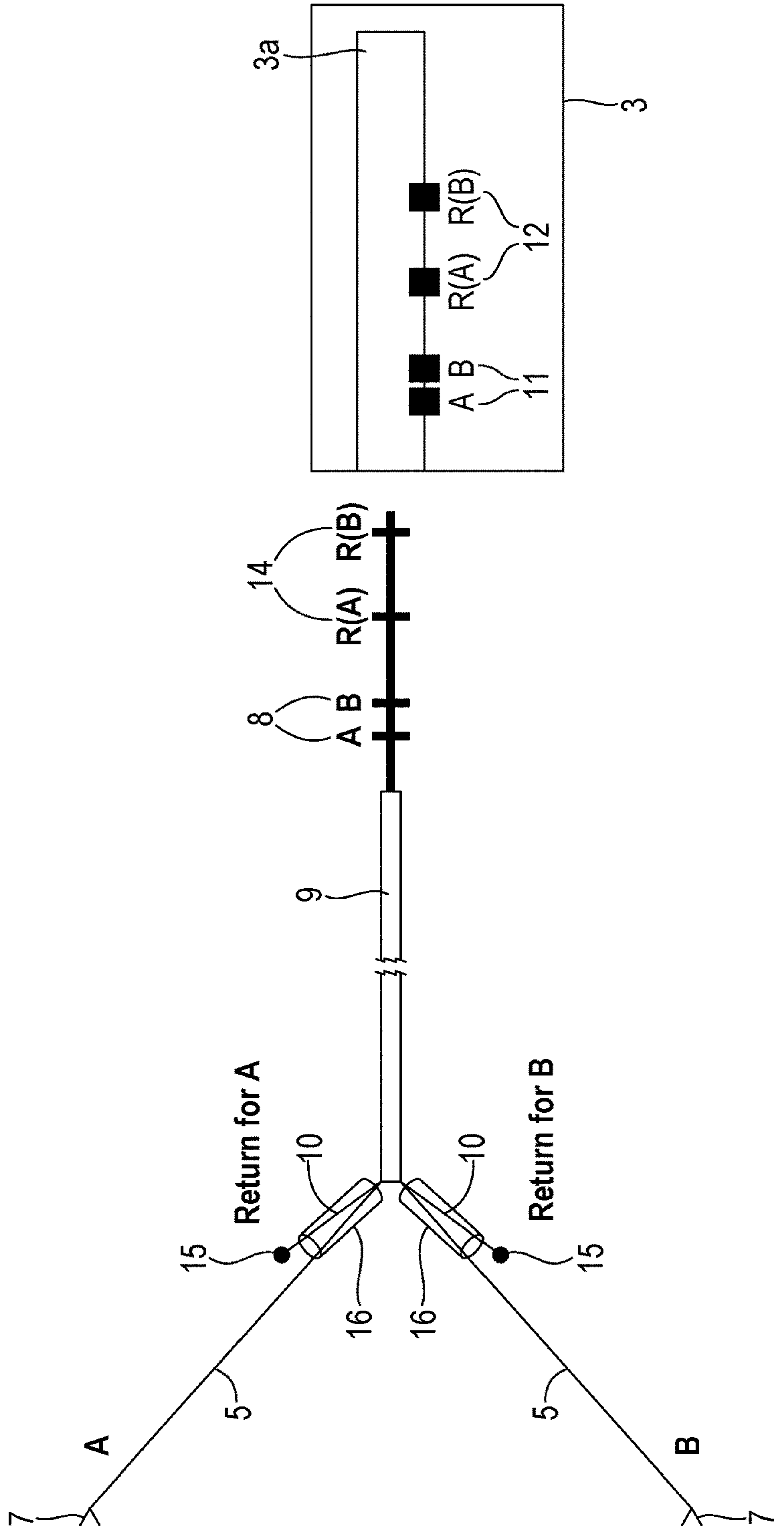
FIG. 3 is a schematic of an embodiment with a pin and two secondary leads and two returns with a corresponding connector to an IPG, or any other device having a socket.

FIG. 3 is a schematic of an embodiment with two secondary leads 5 and two returns 10 that connect a complementary connector 7 to an IPG 3 having an opening 3*a* for connection to the system herein via connectors 8 (A, B) and 14 (R (A) and R (B)). The secondary leads are connected to two secondary connectors 8 which connect to recessed connectors 11 (A, B) in an opening 3*a* in the IPG 3. The two returns are connected to return secondary connectors 14 and connect to additional connectors for the returns 12.

Figure 4:
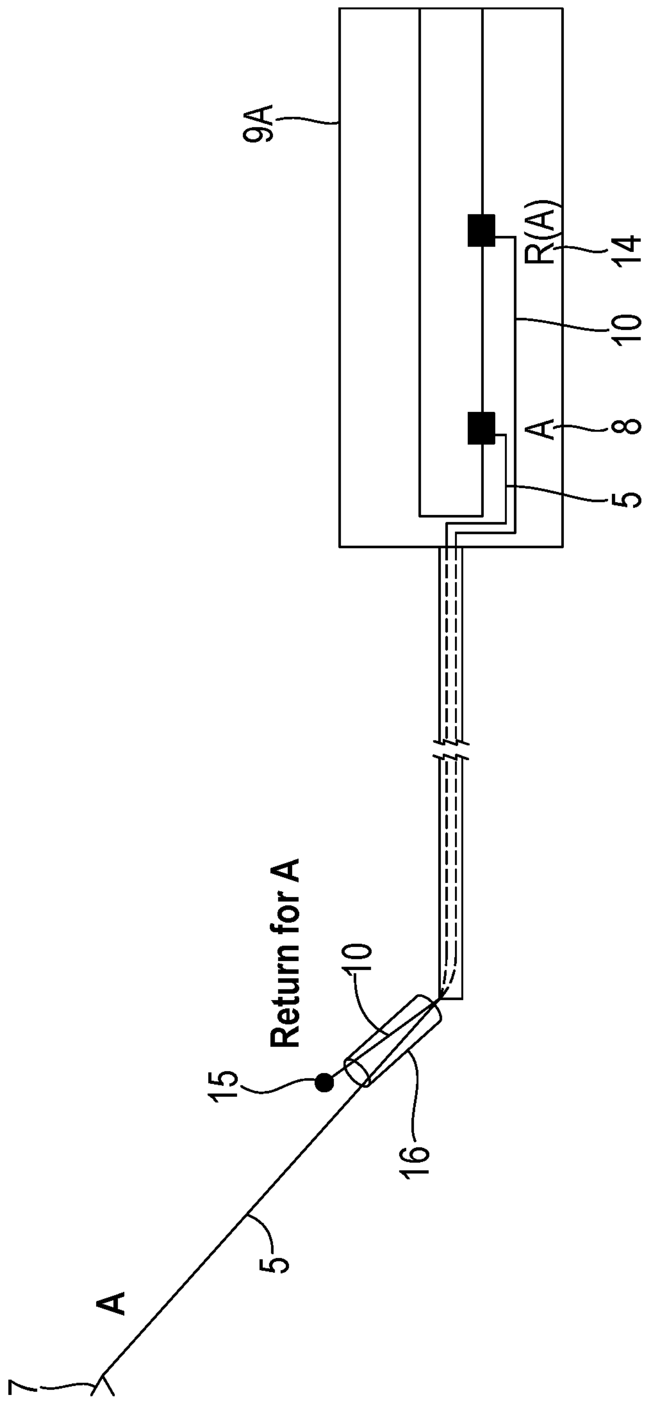
FIG. 4 is a schematic of an embodiment with a socket with single primary and secondary leads and a return with a socket for connecting to a device having a pin.

FIG. 4 is a schematic of an embodiment with a socket connecting to single primary and secondary leads and a return secondary connector 14 in the socket for connecting to a device having a pin. This embodiment differs in character from that in FIG. 3 (apart from reduction of primary and secondary leads from two to one) in that a socket 9A has been substituted for the pin 9 of FIG. 3.

Figure 5A:
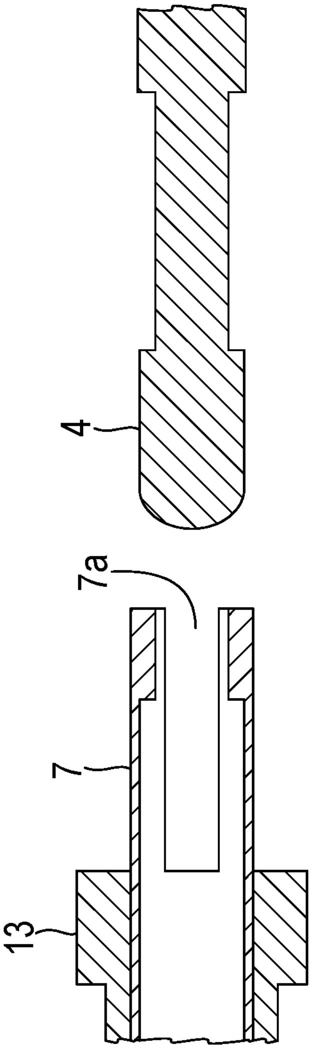
FIG. 5A is a cross-section of an embodiment of a pin and socket connector in a pre-insertion position.
Figure 5B:
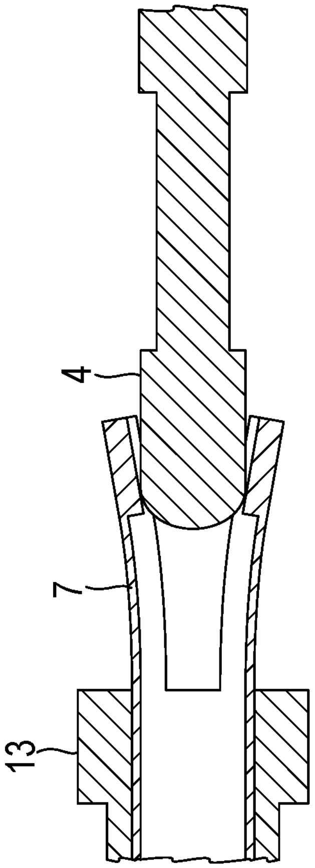
FIG. 5B is a cross section during insertion.
Figure 5C:
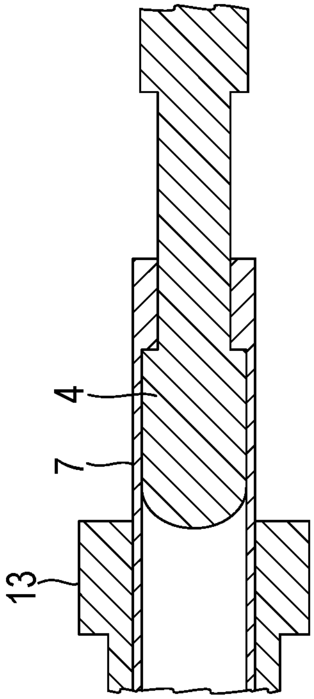
FIG. 5C is post-insertion.

FIG. 5A is a cross-section of an embodiment of a primary connector 4, here a shown as a pin, and a complementary connector 7, here a shown as a socket, in a pre-insertion position. A slot 7*a* allows expansion of the socket for insertion of the pin. FIG. 5B is a cross section during insertion, and FIG. 5C is post-insertion. A docking sleeve 13 can be pushed to the right after insertion to enclose the connectors and to keep them together.

Figures 6A, 6B:
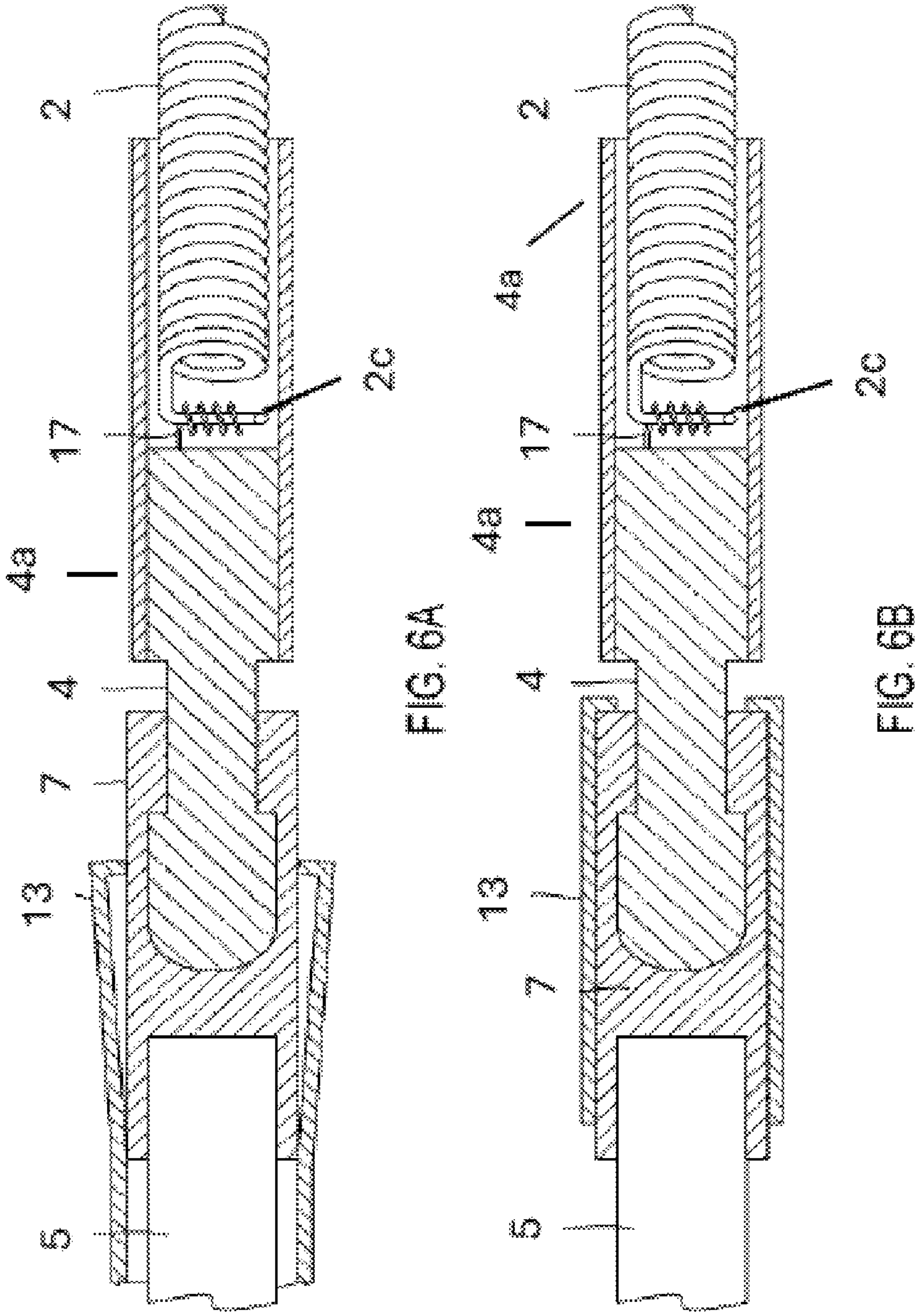
FIG. 6A is one embodiment of a connection between a primary connector and a complementary connector (pin and socket) before the docking sleeve has been moved to cover and to lock them into place.
FIG. 6B is after the docking sleeve has been moved.
Figure 6C:
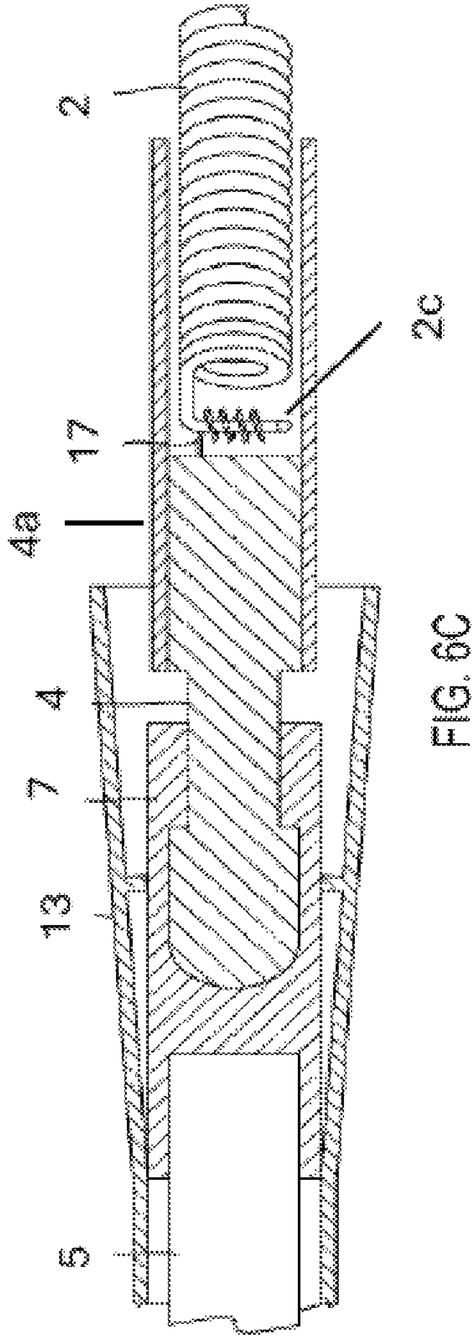
FIGS. 6C and 6D show another embodiment of the docking sleeve before and after locking into place.
Figure 6D:
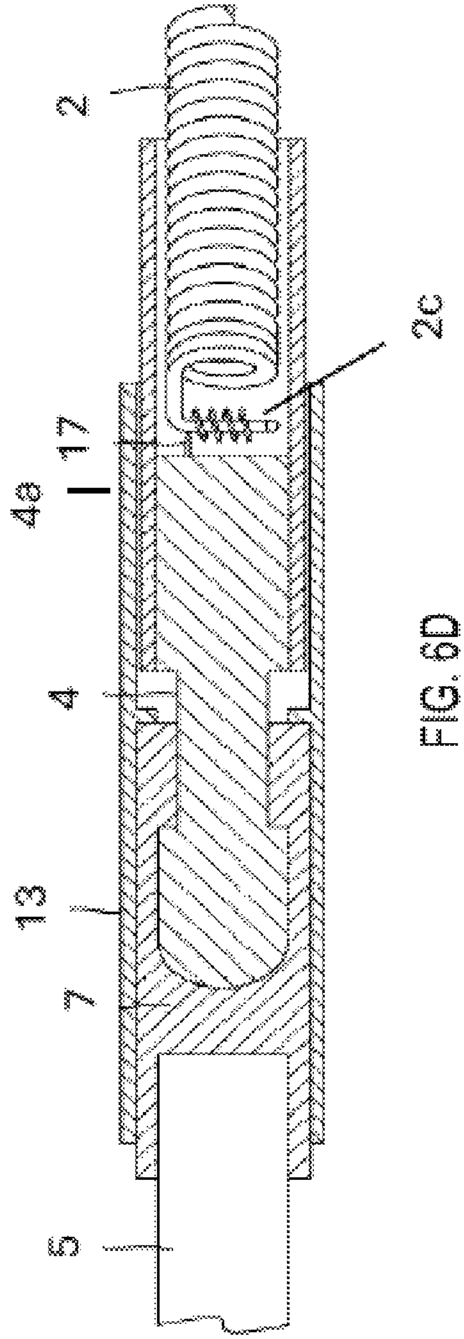

FIG. 6A is a section view of one embodiment of a connection between the complementary connector 7 and the primary connector sleeve 4*a* (socket) before the docking sleeve 13 has been moved to lock them into place, and FIG. 6B is after the docking sleeve has been moved to the locked position. The primary lead 2 is connected to the complementary connector by any secure attachment 17 using a loop-through 2*c*. FIGS. 6C and 6D are additional embodiments.

Figure 7A:
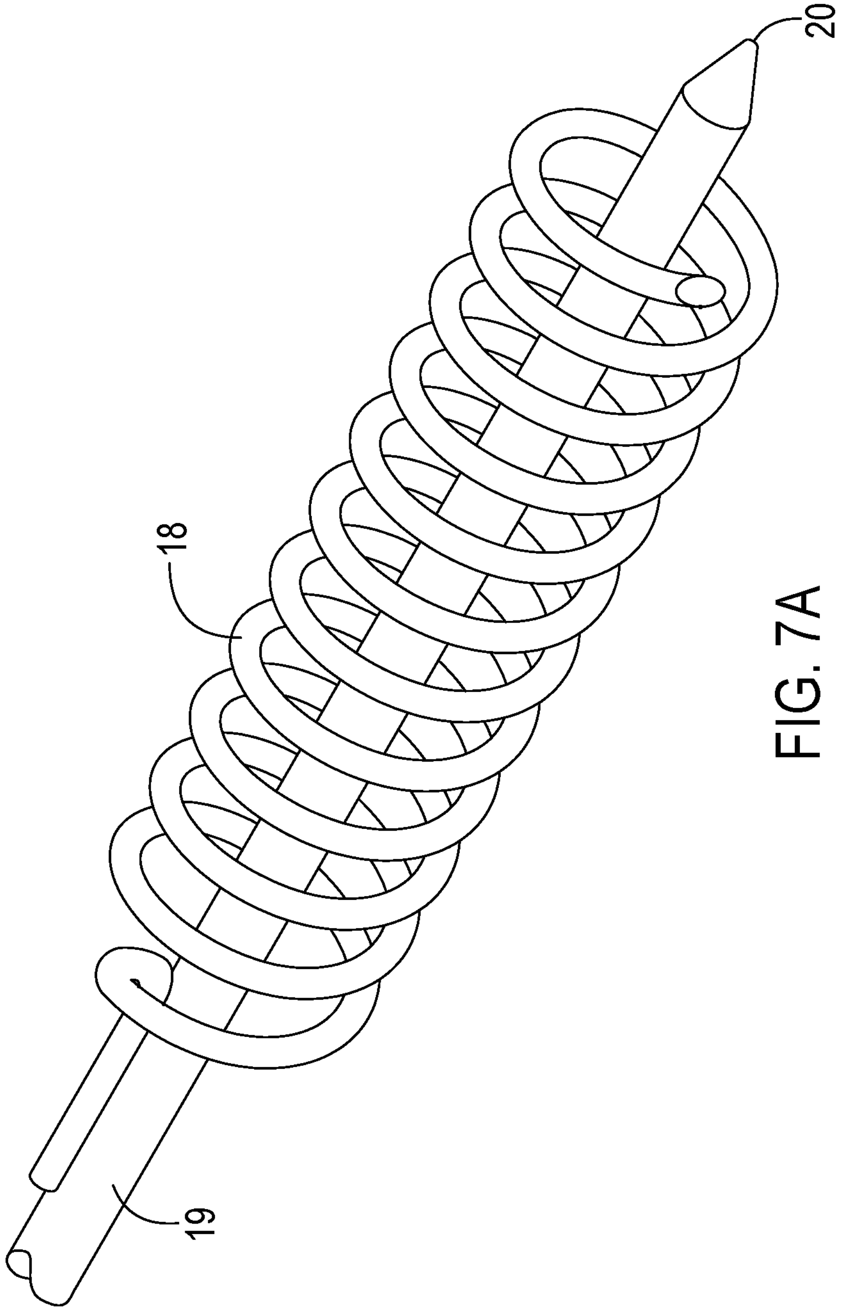
FIGS. 7A and 7B depict an embodiment of the direct connector as a corkscrew, and making a connection with a primary lead.
Figure 7B:
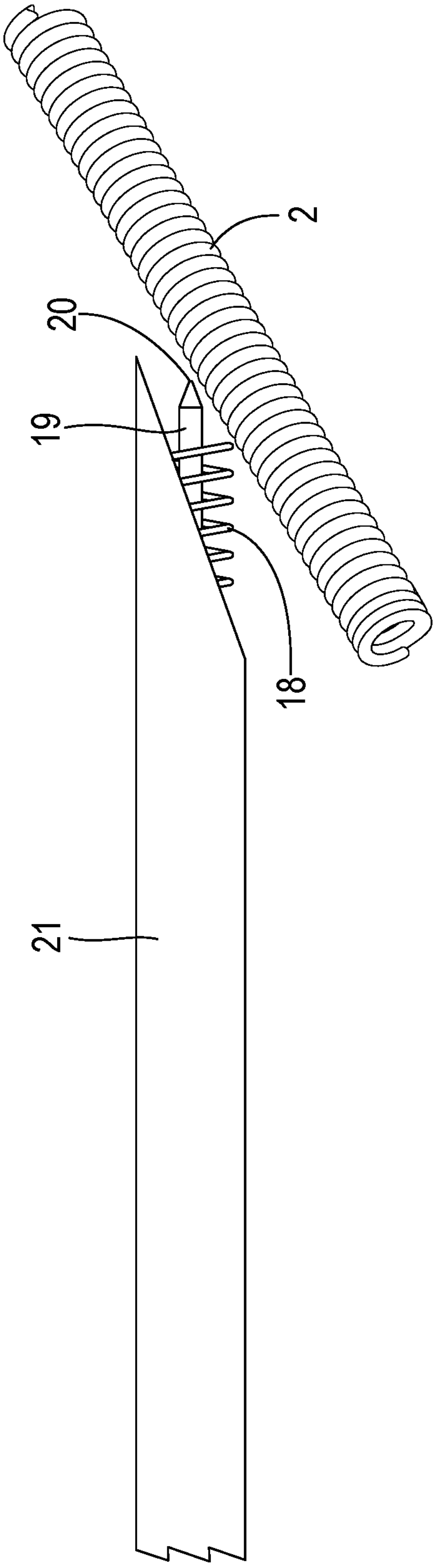

A group of embodiments establishes a direct connection of a previously implanted primary lead anywhere along its length to a lead to an IPG. A "direct connection" in this usage means no modification of the primary lead is needed. The mechanism for a direct connection is selected from the group consisting of a docking coil assembly, a hook and anvil, and a barracuda clip. Other mechanical connectors within this group may also be used. FIGS. 7A and 7B show one of the numerous possible embodiments of the direct connector. The direct connector, comprising a corkscrew and connection needle, is configured for insertion through a cannula (e.g., 14-20 ga) and for mating connections to be made in vivo. Serrations or jaws on the direct connectors can be employed to provide a secure electrical and mechanical connection.

Via a "direct connector to socket adapter" extension scheme, a formerly placed lead with no additional modifications can be directly connected in vivo via a needle based procedure, with multiple connector designs described herein (see method 1). The lead can also be modified to include an integrated 'pin' connector, with methods and designs of securing the wire structure electrode material to the connectors described herein (see method 2). The 'socket' connector is also needle deliverable and extends the wire structure electrode electrical path once connected to the 'pin' end and provides an extended end for other devices to be connected to (see method 3).

FIGS. 7A and 7B depict an embodiment of a direct connector in an embodiment with a corkscrew 18, and making a connection with a primary lead in FIG. 7B. The corkscrew 18 is securely affixed to a connection needle 19, and is inserted through a delivery device 21 to allow the tip and corkscrew to attach to the primary lead 2. The connection needle is attached to a secondary lead 5.

Figure 8:
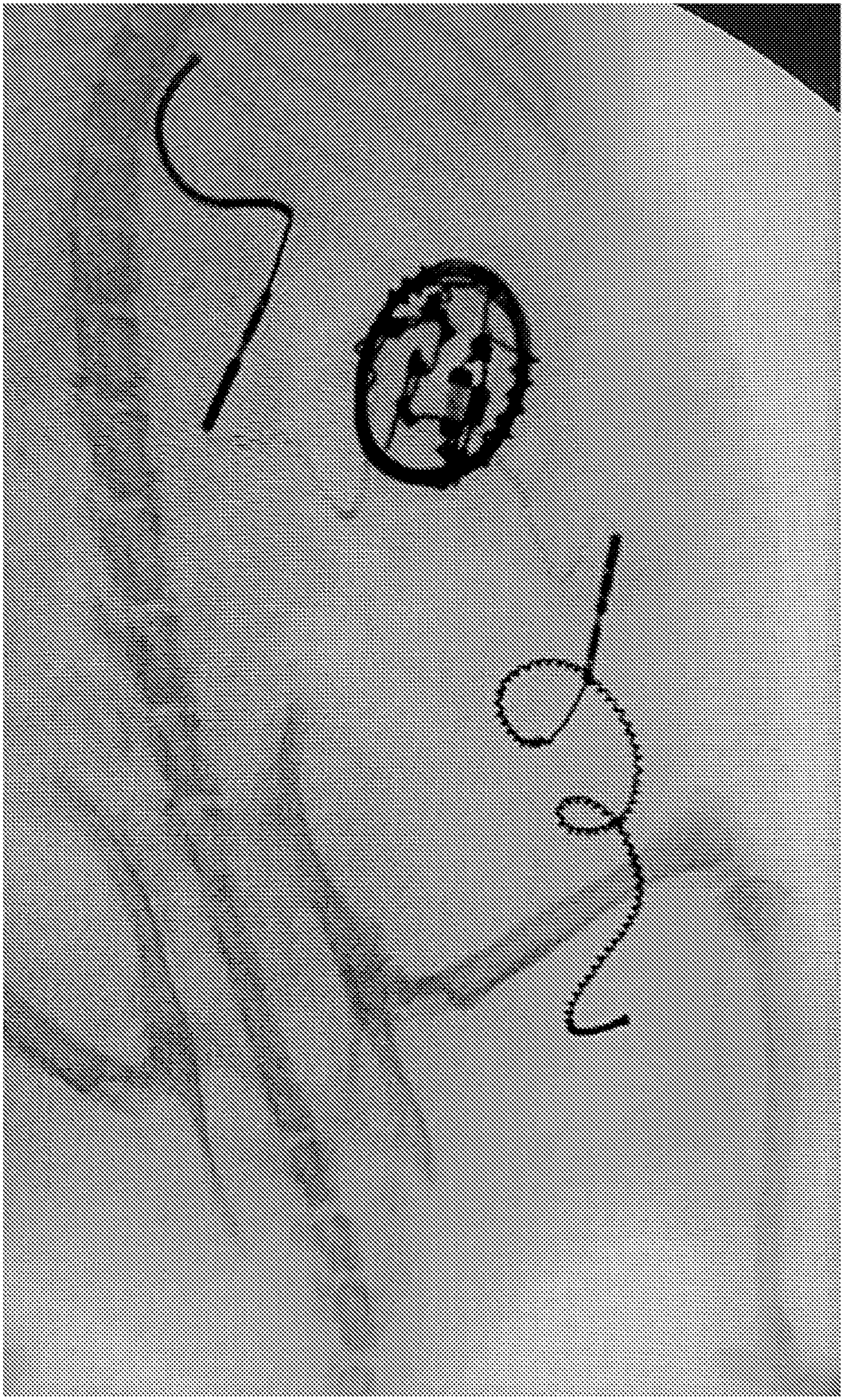
FIG. 8 is an image of two sets of primary and secondary leads connected to an IPG as implanted in an animal.

FIG. 8 is an image of two sets of primary and secondary leads connected to an IPG as implanted in an animal.

A zone of innervation can include nerve fibers which are connected to the spinal cord at different vertebra. So, in various embodiments of the system, the number of leads for interface with the dorsal root ganglion can include two for each vertebra (bilateral) multiplied by the number of vertebra where the nerves for that zone attach to the spinal cord for a total of, say, four or six leads.

Delivery methods are conducted either immediately after placement of the electrode (unmodified or modified), or may be conducted at a later time following electrode implant. Devices to achieve the delivery can include a series of cannulas with inner diameter larger than that of the cannula deliverable connectors and may include a holding mechanism that temporally secures the target connector in place. The holding mechanism has "soft jaws" that clamp around the target connector and restricts axial movement while the interconnect is formed. Once formed, the holding mechanism releases, with the delivery device retracted to allow full deployment of the "extension" devices described.

It must also be understood that the primary lead 2 and the secondary lead 5 may be separate devices. A first device comprises a primary lead 2 having distal and proximal ends 2*a*, 2*b* and a primary connector 4 attached to the proximal end, the device being configured for injecting fully into a body through a delivery device, and further configured such that the distal end 2*a* may be placed near a tissue target and the proximal end 2*a* is configured to pick up energy from a source internal or external to the body as a trial lead, and the primary connector 4 is available to be connected to a complementary connector 7, which may be connected at the same time as the first device is implanted, or at a later time. A second device comprises at least one secondary lead 5 having first and second ends 5*a*, 5*b*, a complementary connector 7 attached to each first end 5*a*, and a secondary connector 8 attached to each second end 5*b* and configured for connection to an IPG 3 or other device, the complementary connector 7 being configured to be connected to a primary connector 4 on a proximal end 2*b* of a primary lead 2 previously placed in a body.

In another embodiment, the second lead comprises a lead such as a helical wire rope structure with a socket connector.

The system may be placed using the following methods.

Method 1 comprises the steps of (1) placing near a tissue target a primary lead with a primary connector at the proximal end, (2) awaiting tissue ingrowth and testing functionality of the primary lead in a wireless stimulation setup, (3) tunneling to the primary connector (under fluoroscopy or ultrasound) and forming a secure hold with the delivery system on to the primary connector, (4) placing the secondary lead with a complementary connector into a cannula and establishing interconnection with the primary connector and (5) disengaging the holding mechanism and retracting the delivery cannula to leave behind the second lead as an extension with an exposed connector end to which additional devices and adapters may then be connected.

Method 2 comprises the steps of (1) placing a primary lead or electrode near a tissue target, (2) awaiting tissue ingrowth and testing its functionality, (3) forming a direct connection (e.g., with a corkscrew connector) to the proximal end of the primary lead using a minimally invasive needle based approach by tunneling to the target (under fluoroscopy or ultrasound), and (4) after placing the direct connector, removing the delivery cannula and connecting an adaptor or implantable stimulation device to be placed in a subcutaneous pocket.

Method 3 comprises the steps of either Method 1 or 2 also immediately after placement of the devices without a period of ingrowth.

Method 4 comprises the steps of Methods 1, 2, or 3, performed in an open cut down, although the minimally invasive cannula based methods are preferable for patient safety and comfort. The placement of an IPG to which the primary lead is connected is performed as an open cut down surgery.

Method 5 comprises the steps of Method 1 or 2 and the additional step of evaluating the usefulness of each of the implanted primary leads and connecting a subset of the implanted primary leads to a secondary lead.

We claim:

1. A system for transferring energy to an at least one target, said system comprising:

an at least one primary lead formed from a and said helical wire rope structure having a helical wire rope structure proximal end and a helical wire rope structure distal end and said helical wire rope structure distal end is an electrode and is proximal to said at least one target;

at least one secondary lead having a secondary lead distal end and a secondary lead proximal end;

a complementary connector having a secure attachment, a primary connector and a primary connector sleeve;

said helical wire rope structure having a loop-through at said helical wire rope structure proximal end;

said helical wire rope structure proximal end inserted into a primary connector sleeve and said loop-through on said helical wire rope structure is attached to said secure attachment forming a connection to said primary connector;

a secondary connector attached to said secondary lead distal end of said at least one secondary lead such that, when said secondary lead distal end of said at least one secondary lead is positioned proximal to said at least one target and said primary connector is joined to said secondary connector and said at least one secondary lead proximal end is attached to a device providing electrical energy, the system provides at least one completed electrical connection between the target and the device providing electrical energy.

2. The system of claim 1 further comprising:

a return for each said primary lead and said return provides at least one completed electrical connection to said electrode.

3. The system of claim 1 comprising:

a plurality of said primary lead and said secondary lead, wherein at least a portion of each of said secondary lead is insulated and said insulated portions of said secondary leads are joined together and said secondary connectors are located on a connecting structure selected from the group of a socket and an insertion pin.

4. A device comprising:

a helical wire rope structure having a helical wire rope structure distal end and a helical wire rope structure proximal end and said helical wire rope structure forming a helical wire rope structure primary lead and a helical wire rope structure electrode and said helical wire rope structure electrode being at said helical wire rope structure distal end and said helical wire rope structure proximal end forming said helical wire rope structure primary lead; and a complementary connector comprising of a primary connector formed from a primary connector sleeve and a secure attachment;

and said helical wire rope structure having a loop-through and said primary connector attached to said helical wire rope structure proximal end using said loop-through and attaching said loop-through to said secure attachment, which is attached to said primary connector, said device configured for injection using a delivery device, and said device further configured such that the helical wire rope structure distal end may be placed near a target, and said primary connector being configured to join to a secondary connector which is attached to an at least one secondary lead and said at least one secondary lead in turn is connectable to a device providing electrical energy to said electrode.

* * * * *